(12) United States Patent
Selvaganapathy et al.

(10) Patent No.: US 10,514,351 B2
(45) Date of Patent: Dec. 24, 2019

(54) SENSORS AND METHODS FOR DETECTING AN OXIDANT

(71) Applicant: McMaster University, Hamilton (CA)

(72) Inventors: Ponnambalam Ravi Selvaganapathy, Dundas (CA); Peter Kruse, Hamilton (CA); Enamul Hoque, Hamilton (CA); Huan-Hsuan Hsu, Ancaster (CA)

(73) Assignee: MCMASTER UNIVERSITY, Hamilton (CA)

( * ) Notice: Subject to any disclaimer, the term of this patent is extended or adjusted under 35 U.S.C. 154(b) by 784 days.

(21) Appl. No.: 14/828,730

(22) Filed: Aug. 18, 2015

(65) Prior Publication Data

US 2016/0047773 A1 Feb. 18, 2016

Related U.S. Application Data

(60) Provisional application No. 62/038,415, filed on Aug. 18, 2014.

(51) Int. Cl.
*G01N 27/12* (2006.01)
*G01N 33/18* (2006.01)

(52) U.S. Cl.
CPC ......... *G01N 27/127* (2013.01); *G01N 33/182* (2013.01)

(58) Field of Classification Search
CPC ......... G01N 27/04–127; G01N 33/182; G01N 33/18–893; G01N 27/127
See application file for complete search history.

(56) References Cited

U.S. PATENT DOCUMENTS

| 6,017,440 A * | 1/2000 | Lewis ................. G01N 27/126 204/403.01 |
| 2008/0093226 A1* | 4/2008 | Briman ................ G01N 27/127 205/775 |

FOREIGN PATENT DOCUMENTS

WO WO-2013033541 A1 * 3/2013 ............. G01N 27/06

OTHER PUBLICATIONS

Teh, et al. ("MEMS sensor material based on polypyrrole-carbon nanotube nanocomposite: film deposition and characterization" Journal of Micromechanics and Microengineering, vol. 15, Sep. 20, 2005, p. 2019-2027. (Year: 2005).*
Hsu, Leo H.H., et al., A carbon nanotube based resettable sensor for measuring free chlorine in drinking water, Applied Physics Letters, 106, Feb. 9, 2015, pp. 063102-1-063102-4.
Srivastava, Subodh, et al,. "Study of chemiresistor type CNT doped polyaniline gas sensor", Synthetic Metals, 160, 2010, 529-534.
(Continued)

*Primary Examiner* — J. Christopher Ball
(74) *Attorney, Agent, or Firm* — Bereskin & Parr LLP/S.E.N.C.R.L., S.R.L.; Patricia Folkins

(57) ABSTRACT

The present application relates to sensors and methods for detecting and/or quantifying an oxidant such as free chlorine in a liquid sample such as drinking water. The sensors comprise a first electrode, a second electrode and a composite material between and connecting the first electrode and the second electrode, the composite material comprising a semiconductor and a redox-switchable organic compound associated therewith. The methods comprise exposing the liquid sample to the sensor under conditions to oxide the redox-switchable organic compound and analyzing a resulting change in current.

19 Claims, 7 Drawing Sheets

(56) References Cited

OTHER PUBLICATIONS

Moonoosawmy, Kevin R., et al., "Cause and Consequence of Carbon Nanotube Doping in Water and Aqueous Media", J. Am. Chem. Soc.,132, 2010, 1572-1577.

Baibarac, M., et al., "Polyaniline and Carbon Nanotubes Based Composites Containing Whole Units and Fragments of Nanotubes", Chem. Mater., 2003, 15, 4149-4156.

Do Nascimento, Gustavo M., et al. "Synthesis and Characterization of Single-Wall-Carbon-Nanotube-Doped Emeraldine Salt and Base Polyaniline Nanocomposites", J. Polym. Sci. Part A Polym. Chem., 43, 2005, 815-822.

* cited by examiner (a)

(b)

(a)

(b)

SENSORS AND METHODS FOR DETECTING AN OXIDANT

CROSS-REFERENCE TO RELATED APPLICATIONS

The present application claims the benefit of priority from U.S. provisional application No. 62/038,415 filed on Aug. 18, 2014, the contents of which are incorporated herein by reference in their entirety.

FIELD

The present application relates to sensors and methods for detecting and/or quantifying an oxidant in a liquid sample.

BACKGROUND

Free chlorine from dissolved chlorine gas is the most common disinfectant used in drinking water due to its high oxidation capacity.

The residual chlorine concentration is typically accurately controlled in a range around 0.5-2 mg/L to avoid both bacterial contamination (free chlorine <0.5 mg/L)[1] and hazard to human health (free chlorine >2 mg/L)[2].

Current standard technology for free chlorine sensing uses reagents which restricts its use to laboratory-based settings[3]. Therefore, free chlorine concentration is typically monitored only at the source of tap water supply. However, monitoring the concentration at many points along the water distribution network, continuously, is useful to guarantee drinking water quality as the free chlorine concentration can be affected by many parameters such as temperature, sunlight and time during water transportation[2].

Known methods for measuring chlorine concentration include, for example, titration (iodometric or amperometric[3]), chemiluminescence and electrochemical methods. Titration-based approaches use reagents which are not suited for continuous or autonomous monitoring. The chemiluminescence method also uses reagents, where the sample is first reacted with chemiluminescent indicators to generate optical signal intensity which is proportional to the concentration of free chlorine in the sample[4-6]. In addition, known chemiluminescent methods use optical light sources and detectors, making it expensive[7]. Electrochemical methods, on the other hand, can be simple in design, do not need additional reactants, and produce sensory signals in an electrical form which is useful for autonomous, continuous monitoring[8-10]. Nevertheless, there are still some common drawbacks of known electrochemical sensors; for example, the sensing results are strongly affected by the flow rate and aging of the electrodes[9,11]; thus, frequent calibration is used.

The controlled modification of the band gaps of single wall carbon nanotubes (SWCNTs) has been applied in various electronic applications[12].

The amphoteric nature of SWCNTs makes it feasible to modify the electronic properties of SWCNTs by doping with either noncarbon atoms or compounds at low concentrations[13-16].

SUMMARY

The present application discloses a sensor for an oxidant that uses oxidation of a redox-switchable organic compound to dope a semiconductor to change its resistance. The oxidation of the redox-switchable organic compound by the oxidant switches the doped semiconductor system into a low resistance (p-doped) state which can be detected by probing with a small voltage. The change in resistance in the presence of oxidants such as chlorine and hydrogen peroxide was found to be proportional to the log-scale concentration of the oxidant in the sample. The p-doping of the doped semiconductor system can then be electrochemically reversed by polarizing it cathodically. This new sensor not only showed good sensing response in a workable concentration range of free chlorine in drinking water, as well as a workable concentration range for hydrogen peroxide, but was also able to be electrochemically reset back many times without the use of any reagents. This simple sensor is useful, for example, for measuring free chlorine in drinking water, for example, in a continuous manner.

Accordingly, the present application includes a sensor for detecting and/or quantifying an oxidant in a liquid sample, the sensor comprising:
(a) a first electrode;
(b) a second electrode opposed to the first electrode; and
(c) a composite material between and connecting the first electrode and the second electrode, the composite material comprising a semiconductor and a redox-switchable organic compound associated therewith,
wherein the sensor detects and/or quantifies the oxidant in the liquid sample by detecting a resistance change in the composite material.

The present application also includes a method for detecting an oxidant in a test liquid sample, the method comprising:
applying a voltage across the first electrode and second electrode of a sensor of the present application in the presence of a blank liquid sample;
obtaining a first current value;
applying the voltage across the first electrode and second electrode of the sensor of the present application in the presence of the test liquid sample; and
obtaining a second current value,
wherein an increase in second current value from the first current value indicates the presence of the oxidant in the test liquid sample.

The present application further includes a method for quantifying the concentration of an oxidant in a test liquid sample, the method comprising:
applying a voltage across the first electrode and second electrode of a sensor of the present application in the presence of the test liquid sample;
obtaining a current value for the test liquid sample; and
comparing the current value for the test liquid sample with current values for one or more standard liquid samples to determine the concentration of the oxidant in the test liquid sample, wherein the current value for the test liquid sample is proportional to the concentration of the oxidant in the liquid sample.

Other features and advantages of the present application will become apparent from the following detailed description. It should be understood, however, that the detailed description and the specific examples while indicating embodiments of the application are given by way of illustration only and the scope of the claims should not be limited by the embodiments set forth in the examples, but should be given the broadest interpretation consistent with the description as a whole.

BRIEF DESCRIPTION OF THE DRAWINGS

The present application will now be described in greater detail with reference to the drawings in which.

DETAILED DESCRIPTION

I. Definitions

Figure 1:
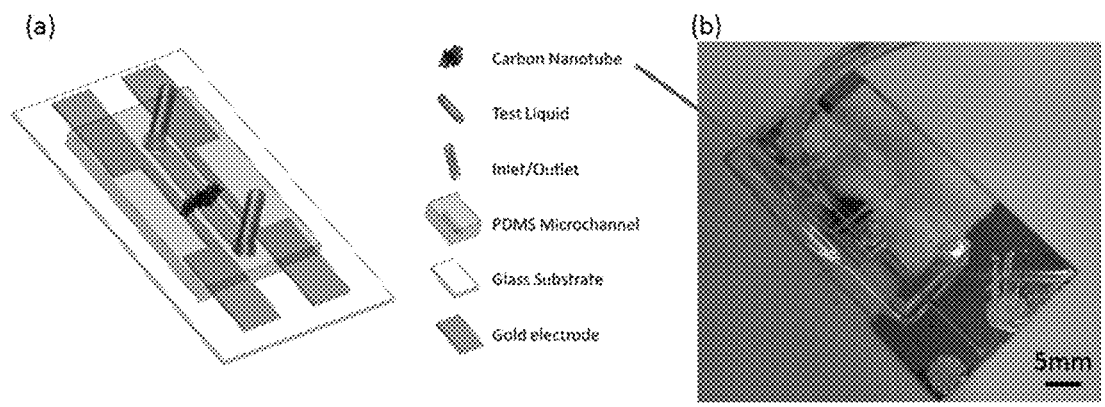
FIG. 1 shows (a) schematics and (b) a photograph of a phenyl capped aniline tetramer-single wall carbon nanotube (PCAT-SWCNT)-based sensor according to an embodiment of the present application.

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "and/or" as used herein means that the listed items are present, or used, individually or in combination. In effect, this term means that "at least one of" or "one or more" of the listed items is used or present.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a semiconductor" should be understood to present certain aspects with one semiconductor or two or more additional semiconductors.

In embodiments comprising an "additional" or "second" component, such as an additional or second semiconductor, the second component as used herein is chemically different from the other components or first component. A "third" component is different from the other, first, and second components, and further enumerated or "additional" components are similarly different.

The term "suitable" as used herein means that the selection of the particular molecule, material and/or conditions would depend on the specific conditions or requirements that need to be met, but the selection would be well within the skill of a person trained in the art. All process/method steps described herein are to be conducted under conditions sufficient to provide the stated product. A person skilled in the art would understand that all process/method conditions, including, for example, solvent, time, temperature, pressure, reactant ratio and whether or not the process or method step should be performed under an anhydrous or inert atmosphere, can be varied to optimize the yield of the desired product and it is within their skill to do so.

The term "redox-switchable organic compound" as used herein refers to an organic compound that is switchable between a reduced form and an oxidized form by the oxidant being analyzed by the sensors for detecting and/or quantifying an oxidant in a liquid sample of the present application or in the methods for detecting and/or quantifying an oxidant in a liquid sample of the present application. The selection of a suitable redox-switchable organic compound for a particular sensor or method of the present application can be made by a person skilled in the art. In an embodiment, the redox-switchable organic compound is reversibly redox-switchable; i.e. the oxidized form of the redox-switchable organic compound is reducible, for example, by electrochemical means back to the original form of the redox-switchable organic compound.

The term "blank liquid sample" as used herein refers to a sample that consists essentially of the same composition as the test liquid sample but which does not comprise the oxidant to be detected.

The term "semiconductor" as used herein includes semi-metals (e.g. graphite and graphene) and combinations of semiconducting, semi-metallic and/or metallic nanoparticles and nanowires in the form of a percolation network.

The term "free chlorine" as used herein refers to both HOCl and OCl$^-$. It will be appreciated by a person skilled in the art that the proportion of each of these species in a solution will depend, for example, on the pH of the solution.

II. Sensors and Devices

Free chlorine from dissolved chlorine gas is widely used as a disinfectant for drinking water. The residual chlorine concentration is continuously monitored and accurately controlled in a certain range around 0.5-2 mg/L to ensure drinking water safety and quality. It would be useful, for example, to have a simple, reliable, and/or reagent-free monitoring device for chlorine in drinking water. Likewise, it would be useful, for example to have a simple, reliable, and/or reagent-free monitoring device for other oxidants in liquid samples.

The present application discloses a sensor for an oxidant that uses oxidation of a redox-switchable organic compound to dope a semiconductor so as to change the semiconductor's resistance. The oxidation of the redox-switchable organic compound by an oxidant switches the doped semiconductor system into a low resistance (p-doped) state which can be detected by probing with a small voltage. The change in resistance was found to be proportional to the log-scale concentration of oxidant in the sample. The p-doping of the doped semiconductor system can then be electrochemically reversed by polarizing the doped semiconductor cathodically. This sensor not only showed good sensing response over a workable concentration range for both free chlorine and hydrogen peroxide, but was also able to be electrochemically reset back many times without the use of any reagents. This simple sensor is useful, for example, for measuring free chlorine in drinking water, for example, in a continuous manner.

Accordingly, the present application includes a sensor for detecting and/or quantifying an oxidant in a liquid sample, the sensor comprising:
(a) a first electrode;
(b) a second electrode opposed to the first electrode; and
(c) a composite material between and connecting the first electrode and the second electrode, the composite material comprising a semiconductor and a redox-switchable organic compound associated therewith, wherein the sensor detects and/or quantifies the oxidant in the liquid sample by detecting a resistance change in the composite material.

The oxidant is any suitable oxidant. In an embodiment, the oxidant is an oxidant used in water treatment. In another embodiment of the present application, the oxidant comprises free chlorine, hydrogen peroxide, chloramines, ozone or combinations thereof. In a further embodiment, the oxidant comprises free chlorine. It is an embodiment that the oxidant comprises hydrogen peroxide.

The sample is any suitable liquid sample. It will be appreciated by a person skilled in the art that the liquid sample includes samples which are originally in a different form but then reconstituted in a suitable liquid prior to testing. In an embodiment, the liquid sample is drinking water. In another embodiment, the liquid sample is from a point along a water distribution network. In a further embodiment of the present application, the liquid sample is wastewater, surface water, lake water or ground water.

In an embodiment, the first electrode, the second electrode and the composite material are provided on a substrate. The substrate comprises or consists essentially of any suitable nonconductive material, that is substantially non-degradable under the conditions described herein, the selection of which can be made by a person skilled in the art. In an embodiment, the substrate comprises or consists essentially of glass, a suitable plastic (e.g. polycarbonate, polypropylene, polyimide, polystyrene or acrylic) or paper. In another embodiment of the present application, the substrate comprises or consists essentially of glass.

In an embodiment, the semiconductor is in the form of a layer that is grown in situ, vapour-deposited, drop-deposited, screen-printed, ink jet-printed, abrasion-deposited or flow-deposited (e.g. on the substrate) between the first and second electrodes. Such means for depositing semiconductor materials are known in the art and the selection of a suitable method for a particular semiconductor (and substrate) can be made by a person skilled in the art.

In an embodiment of the present application, the semiconductor comprises or consists essentially of single wall carbon nanotubes (SWCNTs) and the single wall carbon nanotubes are deposited on the substrate by drop-depositing a suspension of the SWCNTs in a suitable solvent (for example, methanol) between the first and second electrodes under conditions to form a film between and connecting the first electrode and the second electrode.

In another embodiment of the present application, the semiconductor comprises or consists essentially of graphite and the graphite is abrasion-deposited on the substrate using a graphite pencil to write on the substrate thereby depositing graphite flakes between the first and second electrodes so as to connect the first electrode and the second electrode.

The semiconductor layer is any suitable thickness and will depend, for example, on the identity of the semiconductor. In an embodiment, the semiconductor layer is from about 50 μm to about 200 μm or about 100 μm thick.

The electrodes comprise or consist essentially of any suitable material. In an embodiment, the first electrode and second electrode each independently comprise or consist essentially of graphite, gold, silver, copper, aluminium, titanium or indium tin oxide. In another embodiment of the present application, the first electrode and second electrode both comprise or consist essentially of gold. In embodiments of the present application wherein the sensor comprises a substrate, the electrodes are deposited on the substrate by any suitable means. Such means are known in the art and the selection of a suitable means can be made by a person skilled in the art. For example, in an embodiment of the present application, a thin layer (for example, about 100 nm to about 300 nm or about 200 nm thick) of the material the electrode comprises or consists essentially of (for example, gold) is sputter-deposited on a surface of the substrate, and then the desired electrode shape is obtained (for example a width of about 0.5 mm to about 5 mm or about 1 mm) by photolithography.

In an embodiment, the resistance between the electrodes is in the range of from about 0.5 kΩ to about 3 kΩ. However, it will be appreciated by a person skilled in the art that higher resistances can also be used.

The semiconductor comprises or consists essentially of any suitable material. In an embodiment, the semiconductor comprises or consists essentially of carbon. For example, in an embodiment, the semiconductor comprises or consists essentially of carbon nanotubes (e.g. single wall carbon nanotubes (SWCNTs) or multi wall carbon nanotubes (MWCNTs)), graphene, graphite or fullerenes. In another embodiment, the semiconductor comprises or consists essentially of carbon nanotubes. In a further embodiment, the semiconductor comprises or consists essentially of single wall carbon nanotubes (SWCNTs). It is an embodiment that the semiconductor comprises or consists essentially of graphite. In another embodiment, the semiconductor comprises or consists essentially of an inorganic material. For example, in an embodiment, the semiconductor comprises or consists essentially of iron oxide ($Fe_2O_3$) or molybdenum disulfide ($MoS_2$). In a further embodiment, the semiconductor comprises or consists essentially of carbon nanotubes, graphene, graphite, fullerenes, iron oxide ($Fe_2O_3$) or molybdenum disulfide ($MoS_2$).

In an embodiment, the redox-switchable organic compound is associated with the semiconductor by physisorption, chemisorption, covalent attachment or ionic interaction. The redox-switchable organic compound is associated with the semiconductor by any suitable means. In an embodiment, the semiconductor is subjected to a solution of the redox-switchable organic compound in a suitable solvent (for example, methanol) under conditions to associate the redox-switchable organic compound with the semiconductor, for example, a time of about 1 minute to about 1 hour or about 5 minutes at a temperature of about 15° C. to about 40° C. or about 25° C.

The redox-switchable organic compound is any suitable redox-switchable organic compound. In an embodiment, the redox-switchable organic compound is an aniline oligomer or a pyrrole oligomer or polymer. In another embodiment, the redox-switchable organic compound is phenyl capped aniline tetramer (PCAT), amine capped aniline tetramer (ACAT), N,N'-diphenyl-p-phenylenediamine (DPPD) or pyrrole oligomers. In a further embodiment, the redox-switchable organic compound is phenyl capped aniline tetramer (PCAT). In another embodiment, the redox-switchable organic compound is amine capped aniline tetramer (ACAT). In a further embodiment, the redox-switchable organic compound is N,N'-diphenyl-p-phenylenediamine (DPPD).

In an embodiment, the sensor further comprises a microchannel for entry and exit of the liquid sample, the microchannel being in fluid contact with at least a portion of the composite material and not the first electrode and the second electrode. The microchannel can be made by any suitable means, the selection of which can be made by a person skilled in the art. In an embodiment, the microchannel is made by a method comprising conventional soft lithography. In another embodiment of the present application, the microchannel comprises or consists essentially of polydimethylsiloxane (PDMS). In another embodiment, the microchannel has a length of from about 5 mm to about 25 mm or about 15 mm, a width of from about 1 mm to about 3 mm or about 2 mm and a thickness of about 1 mm to about 3 mm or about 2 mm. In a further embodiment, the microchannel is bonded to the substrate using air plasma.

In an embodiment, the sensor further comprises an insulator layer located between the first and second electrodes and the composite material. In another embodiment, the insulator layer comprises or consists essentially of silicon oxide, silicon nitride or paraffin wax. Means for depositing such materials to form such an insulator layer are known to persons skilled in the art.

In an embodiment, the sensor further comprises a counter electrode, reversibly couplable to the first or the second electrode. The counter electrode comprises or consists essentially of any suitable material. In an embodiment, the counter electrode comprises or consists essentially of copper.

It will be appreciated by a person skilled in the art that standard means for applying potential and measuring current can be used for the sensors of the present application. In an embodiment, the sensor is used in a configuration that comprises a series connection of power supply, resistance and ammeter.

The present application also includes a device for detecting and/or quantifying an oxidant in a liquid sample comprising a sensor of the present application. It will be appreciated by a person skilled in the art that embodiments of the sensors for use in the devices of the present application can be varied as detailed herein for the embodiments of the sensors of the present application.

III. Methods

The present application discloses a method for detecting and/or quantifying an oxidant in a liquid sample. The methods use a sensor for an oxidant that uses oxidation of a redox-switchable organic compound to dope a semiconductor and to change its resistance. The oxidation of the redox-switchable organic compound by the oxidant switches the doped semiconductor system into a low resistance (p-doped) state which can be detected by probing with a small voltage. The change in resistance was found to be proportional to the log-scale concentration of the oxidant in the sample. The p-doping of the doped semiconductor system can then be electrochemically reversed by polarizing it cathodically. This sensor not only showed good sensing response over a workable concentration range of the oxidants but was also able to be electrochemically reset back many times without the use of any reagents. This simple sensor is useful, for example, for measuring free chlorine in drinking water, for example, in a continuous manner.

Accordingly, the present application also includes a method for detecting an oxidant in a test liquid sample, the method comprising:
  applying a voltage across the first electrode and second electrode of a sensor of the present application in the presence of a blank liquid sample;
  obtaining a first current value;
  applying the voltage across the first electrode and second electrode of the sensor of the present application in the presence of the test liquid sample; and
  obtaining a second current value,
  wherein an increase in second current value from the first current value indicates the presence of the oxidant in the test liquid sample.

The present application further includes a method for quantifying the concentration of an oxidant in a test liquid sample, the method comprising:
  applying a voltage across the first electrode and second electrode of a sensor of the present application in the presence of the test liquid sample;
  obtaining a current value for the test liquid sample; and
  comparing the current value for the test liquid sample with current values for one or more standard liquid samples to determine the concentration of the oxidant in the test liquid sample, wherein the current value for the test liquid sample is proportional to the concentration of the oxidant in the liquid sample.

It will be appreciated by a person skilled in the art that embodiments of the sensors for use in the methods of the present application can be varied as detailed herein for the embodiments of the sensors of the present application.

The voltage applied across the electrodes is any suitable voltage. It will be appreciated by a person skilled in the art that the voltage applied across the electrodes will depend, for example, on the resistance. For example, for semiconductors having a higher resistance, a higher potential is typically applied across the electrodes. Further, for example, it will be appreciated by a person skilled in the art that for oxidants with a lower oxidation capacity, a higher voltage may be used to amplify the current response. In an embodiment, the oxidant is free chlorine, the semiconductor comprises or consists essentially of SWCNTs and the voltage is about 0.05 mV to about 0.5 mV or about 0.1 mV. In another embodiment of the present application, the oxidant is hydrogen peroxide, the semiconductor comprises or consists essentially of SWCNTs and the voltage is about 0.5 mV to about 5 mV or about 1 mV. In a further embodiment, the oxidant is free chlorine, the semiconductor comprises or consists essentially of graphite and the voltage is about 5 mV to about 15 mV or about 10 mV.

In the methods of the present application, the sensors of the present application can be reset using the sample fluid itself rather than a specialized reference fluid. Accordingly, in another embodiment, the method further comprises, after measuring the current for the test liquid sample, applying a reset voltage across a counter electrode and either the first or second electrode under conditions to reduce the redox-switchable organic compound.

The reset voltage is any suitable reset voltage and will depend, for example, on the identity of the redox-switchable organic compound. In a further embodiment, the reset voltage is about −1.2 V to about +1.2 V or about −0.8 V.

In an embodiment, the method is for continuous monitoring of the oxidant. In another embodiment, the method is for continuous monitoring of the oxidant (for example, free chlorine) along a water distribution network.

In an embodiment, the concentration of free chlorine in the test liquid sample is from about 0.06 mg/L to about 60 mg/L or about 0.06 mg/L to about 6 mg/L. In a further embodiment, the test liquid sample is substantially free of nitrate. In an alternative embodiment of the present application, the test liquid sample comprises both free chlorine and nitrate and the method further comprises using a sensor of the present application in combination with a sensor that is specific for nitrate. Such nitrate sensors are known in the art.

In another embodiment, the concentration of hydrogen peroxide in the test liquid sample is from about 0.05 mg/L to about 5 mg/L.

In an embodiment of the method for quantifying the concentration of an oxidant in a test liquid sample one or more standard liquid solutions are used to calibrate the sensor. In an embodiment, the standard liquid solutions comprise a known quantity of the oxidant and a correlation between the concentration of the oxidant in 2 to 20, or 3 to 10, standard solutions and the current value of the sensor of the present application is established and used to calibrate the instrument to determine the concentration in the test liquid sample. In an embodiment, the correlation or calibration is represented using a graph or a table or is contained in a database. In another embodiment, the correlation or calibration is encoded into software utilized by the sensor. In an embodiment, the sensor is non-portable. In an alternative embodiment, the sensor is portable, for example, the sensor is incorporated into a handheld device.

The following non-limiting examples are illustrative of the present application:

EXAMPLES

Example 1

PCAT-SWCNT Based Chlorine Sensor

Using Raman spectroscopy, the charge transfer induced doping/un-doping reversible switching mechanism of SWCNT networks has been observed by applying an aniline oligomer (phenyl capped aniline tetramer (PCAT)) as the dopant.[17] Normally, the PCAT-SWCNT is undoped, and the resistance of it will be similar to the resistance of the SWCNT. When the PCAT is oxidized, it removes some of the charge from the SWCNT and p-dopes it. This reduces the electrical resistance of the PCAT-SWCNT. Thus, the oxidation and reduction of PCAT can switch the PCAT-SWCNT system back and forth between low resistance (p-doped) and high resistance (un-doped) states.

While not wishing to be limited by theory, the resistance change between the p-doped and un-doped PCAT-SWCNTs is attributed to the change in the chemical structure of the reduced and oxidized PCAT. The oxidized PCAT has a more conjugated structure, thus a smaller HOMO/LUMO gap than the reduced PCAT.[17, 20] The HOMO/LUMO gap of organic molecules can also be electrochemically measured by cyclic voltammetry.[21]

The gap between the oxidation and reduction peak indicates the HOMO/LUMO gap. Cyclic voltammetry of PCAT/SWCNT showed that the HOMO/LUMO gap of the oxidized state was smaller than the reduced state which would result in a reduced resistance.

These resistance changes can be applied to sensing free chlorine since it is a strong oxidant. When chlorine-containing water flows, for example, in a microchannel of the sensors of the present studies, it oxidizes the PCAT and the resistance of PCAT-SWCNTs is lowered which can be measured.

A schematic of the sensor design is shown in FIG. 1(a) and a photograph of the sensor used in the present studies is shown in FIG. 1(b). A commercially available power supply was used for both applying potential and measuring current in the experiments described herein.

The sensor device is composed of two parallel gold electrodes connected by a phenyl capped aniline tetramer (PCAT)-doped single wall carbon nanotube (SWCNT) film and a single microchannel across the PCAT-SWCNT film that brings the sample in contact with the film while preventing its contact with the gold electrodes directly. The device was fabricated by first sputter depositing a thin gold layer (thickness=200 nm) on a glass slide and photolithographically patterning it into the desired electrode shape (thinnest width=1 mm) with a 1 mm spacing in between. Then 200 µL of a SWCNT suspension in methanol was drop deposited between two gold electrodes which forms a film of about 100 µm thickness connecting the two gold electrodes. The resistance between the two electrodes was typically in the range of 0.5-3 kΩ. However, higher resistances can also be used for sensing purposes. Subsequently, a polydimethylsiloxane (PDMS) microchannel (length:width:thickness=15 mm:2 mm:2 mm) made by conventional soft lithography[18] was bonded on top of the glass substrate by air plasma. PCAT in methanol (PCAT:methanol=1:10 ratio by weight) solution (2 mL) was flowed through the PDMS channel in order to adsorb the PCAT onto the SWCNT film.

Then, the device was left to sit for 5 minutes to allow the PCAT molecules to bond to the SWCNT film by the van der Waals force.

The device was studied by flowing 2 mL of free chlorine solution through the microchannel at a flow rate of 0.1 mL/min. The chlorine solutions were prepared by diluting a commercially available chlorine bleach solution (LAVO, Montréal). Four different concentrations of free chlorine solutions were tested: 0.06 mg/L (or ppm), 0.6 mg/L (or ppm), 6 mg/L (or ppm) and 60 mg/L (or ppm) which covers the whole range of free chlorine concentrations commonly present in drinking water. A test potential of 0.1 mV was applied across the PCAT-SWCNTs through the two gold electrodes and the resulting current was measured. The applied potential of 0.1 mV ensured that there was no other electrochemical reaction at the SWCNT-water interface.

Figure 2:
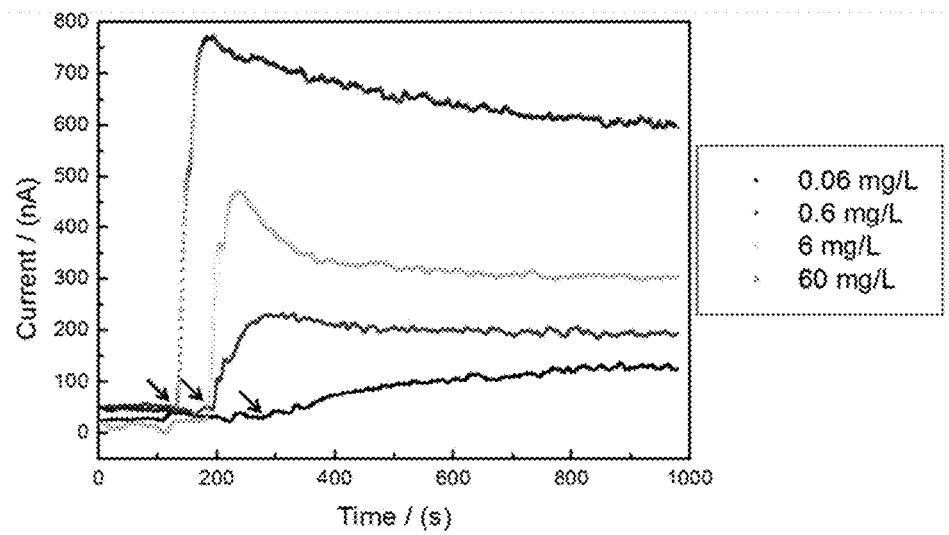
FIG. 2 shows (a) a plot of current (nA) vs time (s) in a sensing device for solutions with a chlorine concentration of 0.06 mg/L to 60 mg/L (from bottom to top of plot) according to an embodiment of the present application. Arrows represent the injection of the chlorine solution. (b) the relationship between the log chlorine concentration and the current which is linear (solid line) for the chlorine concentrations between 0.06 to 6 mg/L of FIG. 2(a) ($R^2$=0.9767). The dotted line between 6 to 60 mg/L represents the non-linear relationship of the log chlorine concentration and the current in that range.
Figure 2:
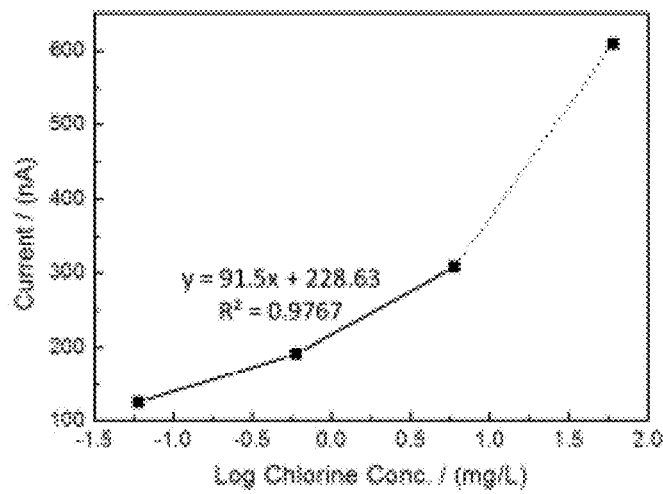

As shown in FIG. 2(a), the results demonstrate a significant increase in the current through the PCAT-SWCNT layer once it comes in contact with free chlorine in the sample solution. The current is stable below 50 nA before the sample solution was introduced. It then increased sharply upon the initial contact and settled down to a stable value around at 125 nA for 0.06 mg/L, 190 nA for 0.6 mg/L, 300 nA for 6 mg/L and 612 nA for 60 mg/L, respectively.

It was found that the measured current is linearly proportional to the log of the chlorine concentration in the range of 0.06-6 mg/L (solid line) and this relationship is shown in FIG. 2(b). This result indicates that the amount of chlorine in the solution is strongly related to the oxidation of the PCAT and consequently the degree of doping of the SWCNTs which leads to changes in the resistance of the PCAT-SWCNT layer. Hence, the current readings can be used to distinguish various free chlorine concentrations.

The reading of the 60 mg/L chlorine sample (dotted line) did not follow the linear relationship established earlier. While not wishing to be limited by theory, this result suggests that at a higher chlorine concentration of 60 mg/L, other mechanisms such as direct oxidation of the SWCNT system may also play a role in doping that could lead to higher sensitivity. Nevertheless, the linear semi-log range (0.06-6 mg/L) of this sensor covers the full range of chlorine concentration for a chlorine sensor to be used in drinking water (0.5-2 mg/L).

Experiments performed on similarly deposited SWCNT films without PCAT did not show a change in resistance to the flow of oxidizing species in the microchannel.

The act of sensing the free chlorine concentration oxidises the PCAT molecules and therefore, the sensor may be regenerated by reducing it before it can be used further. Therefore, resetting the sensor electrochemically was investigated so that the sensor can be reused multiple times.

Figure 3:
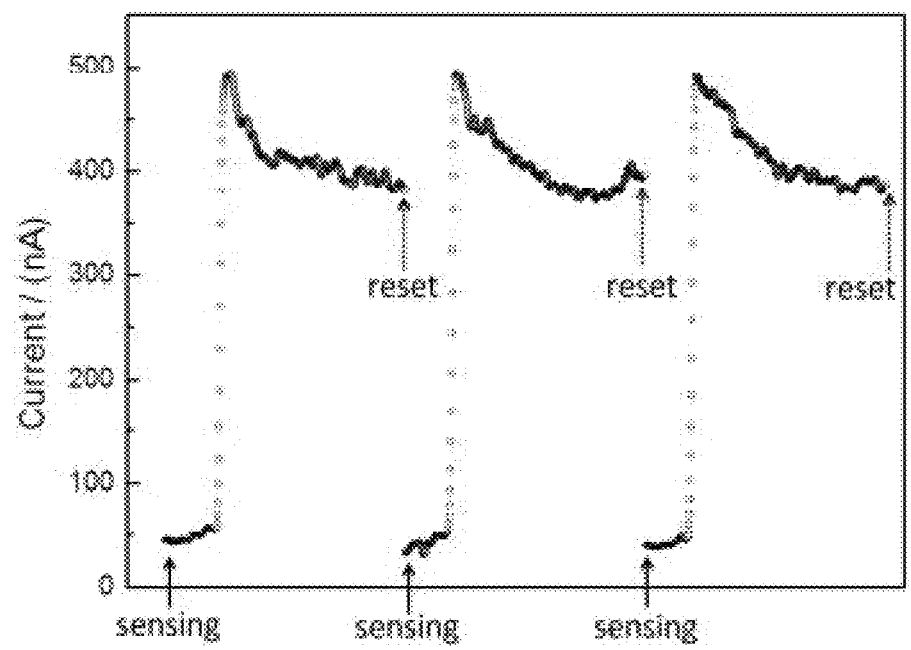
FIG. 3 shows plots demonstrating the resetting of a sensing device according to an embodiment of the present application by applying −0.8 V across one of the gold electrodes and the inlet of solution that de-dopes the PCAT-SWCNTs switching back the current readings to residual value. The reset process was tested by successive oxidation and reduction of the sensing device for a 60 mg/L free chlorine solution. The reset test was repeated three times to examine the reproducibility of the reset process. The triplicate experimental results are plotted both in (a) a successive and (b) an overlapping pattern.
Figure 3:
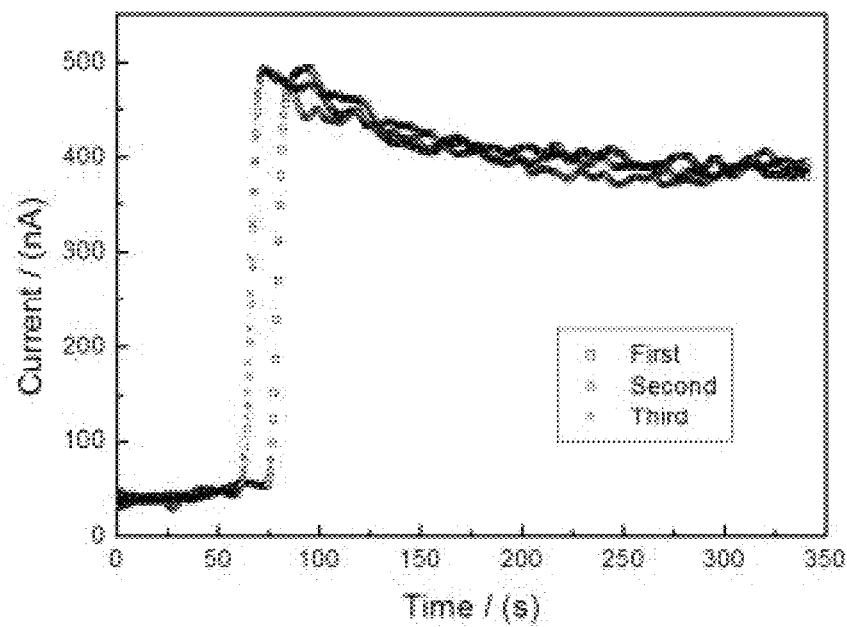

The p-doped PCAT-SWCNTs can be polarized cathodically and be electrochemically un-doped to regain its original resistivity. The "reset" of the sensing device was performed by applying –0.8 V for 5 minutes between one of the gold electrodes and a copper counter electrode placed in the outlet of the microchannel. This procedure reduces the PCAT molecules, un-doping the SWCNTs which regenerates the current reading of PCAT-SWCNTs to the original stage (below 50 nA). The reset test was repeated three times in order to examine the reproducibility of this reset process. The current measurement during the whole process of chemical sensing and electrochemical resetting, repeated three times, is shown in FIG. 3(a). The results suggest that the resistance can be switched back and forth from the original (high) level to the oxidized (low) level by the sensing and reset processes. This ability to reset the device in a reagent free manner allows the CNT sensing device to be applied as an autonomous device for continuous monitoring of free chlorine.

The current vs time characteristic plot of three individual p-doped/reset cycles is also shown in FIG. 3(b). The results show the similar response in each independent experiment, which demonstrates the excellent repeatability of the sensing output from the device.

Since pure water has very low conductivity; the reset was performed in methanol to prevent any contamination of the device. The reset of this sensor in tap water itself rather than methanol was also investigated in order to make it reagent free. It was found that it was possible to reset the sensor in tap water, but due to presence of free chlorine, the PCAT oxidizes and the current increases immediately, reaching a stable value indicative of the free chlorine concentration in it. Nevertheless, this experiment demonstrates that the sensor can be reset both in methanol as well as in water.

In summary, an inexpensive, autonomous device was been demonstrated for continuous monitoring of residual chlorine concentration in drinking water which is based on the oxidation and reduction of PCAT molecule so as to dope and un-dope PCAT-SWCNTs. This device has sufficient sensitivity and detection range (0.06-60 mg/L) to measure the safety of the chlorine level contained in drinking water. In addition, cathodic polarization of p-doped PCAT-SWCNTs after the sensing was found to electrochemically reset it back to the un-doped state so that it can be used for subsequent sensing. No significant variation in conductivity was found after 30 h of experiments, which suggest that the SWCNT film is stable over a reasonable time frame over which it was tested. Since this device is sensitive to the oxidant strength of test solution and not selective to free chlorine alone, the interference from other oxidant species may be possible. Nevertheless, this sensor is useful, for example, for measuring free chlorine along the water distribution network as drinking water is highly controlled and the only oxidant species allowed is free chlorine.[19]

Example 2

Effect of Interfering Species on the Sensor

Figure 4:
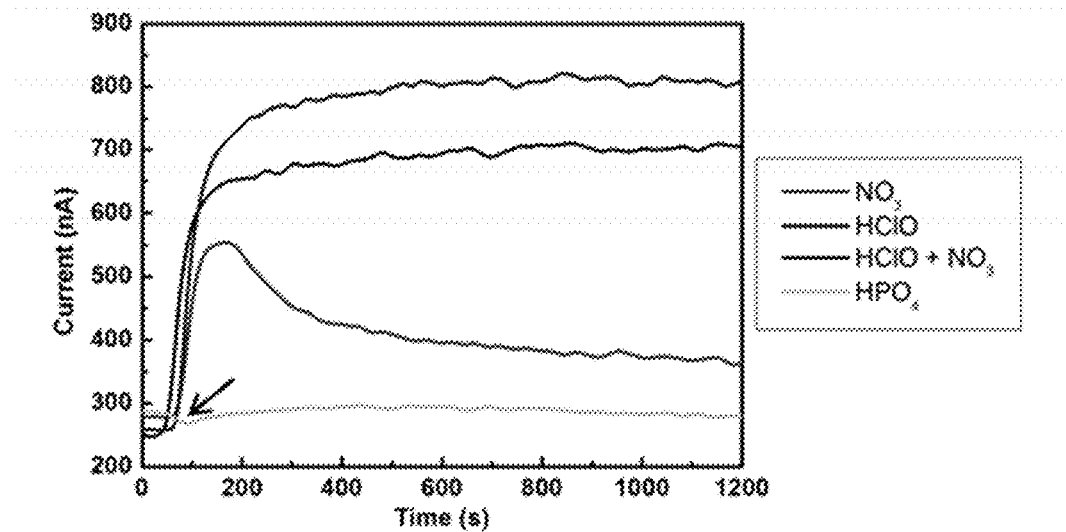
FIG. 4 shows a plot of current (nA) vs. time (s) in a sensing device according to an embodiment of the present application for solutions with 60 ppm $NO_3^-$ (second line from bottom), 100 ppm $HPO_4^{2-}$ (bottom line), 60 ppm HClO (second line from top) and a mixture of 60 ppm $NO_3^-$ and 60 ppm HClO (top line). The arrow in the plot represents the injection of the solution.

Many other anions such as nitrate ($NO_3^-$), sulphate ($SO_4^{2-}$), chloride ($Cl^-$) and bromide ($Br^-$) are also present at varying concentrations in environmental samples and may cause a non-specific response in the sensor which is considered to be an interference. FIG. 4 shows the response of the sensor individually in solutions containing nitrate (60 ppm), phosphate (100 ppm) and free chlorine (HClO; 60 ppm) as well as the combination of nitrate and free chlorine. Nitrate and phosphate are both common anionic species which may be present in natural water thus were selected as the interference. Other experimental setups such as flow rate (0.1 mL/min) and applied potential (0.1 mV) remained identical as the free chlorine sensing described in Example 1.

As shown in FIG. 4, free chlorine (HClO) alone produces a signal of 450 nA. The phosphate ($HPO_4^{2-}$) does not produce a significant measurable response on its own. However, nitrate ($NO_3^-$) can produce a small non-specific signal of 100 nA. This interference is additive and when free chlorine and nitrate are combined the current is a sum (550 nA) of the individual currents. Other common anions such as $SO_4^{2-}$, $Cl^-$, $Br^-$ also showed a similar response to $HPO_4^{2-}$ indicating that other than nitrate, the sensor is very specific to free chlorine.

These results indicate that this sensor can be used either alone (for example, in samples that have a low nitrate concentration) or in combination with a conventional nitrate sensor (for example, in samples with very high nitrate concentrations) to specifically detect free chlorine.

Example 3

Alternative Substrate (Graphite)

In addition to carbon nanotubes such as single wall carbon nanotubes, other substrates such as graphene and graphite can be doped by phenyl-capped oligomers and used as sensors. In the present studies, a sensor was made from pencil graphite. The sensor was fabricated by first sputtering two gold electrodes with a 2 mm separation and a 200 nm thickness on a frosted glass slide. These two gold electrodes were then connected by a graphite film. The graphite film was obtained by manually writing a 1 mm wide line with a 9B (>90% graphite) pencil on the frosted glass slide until the resistance of this line was about 1-3 k$\Omega$. A microfluidic channel was attached to the fabricated graphite sensor in a process similar to the preparation procedures for the SWCNT device described hereinabove in Example 1. Next, the PCAT solution was flowed through the channel and brought into contact with the graphite film to adsorb the PCAT onto it.

Figure 5:
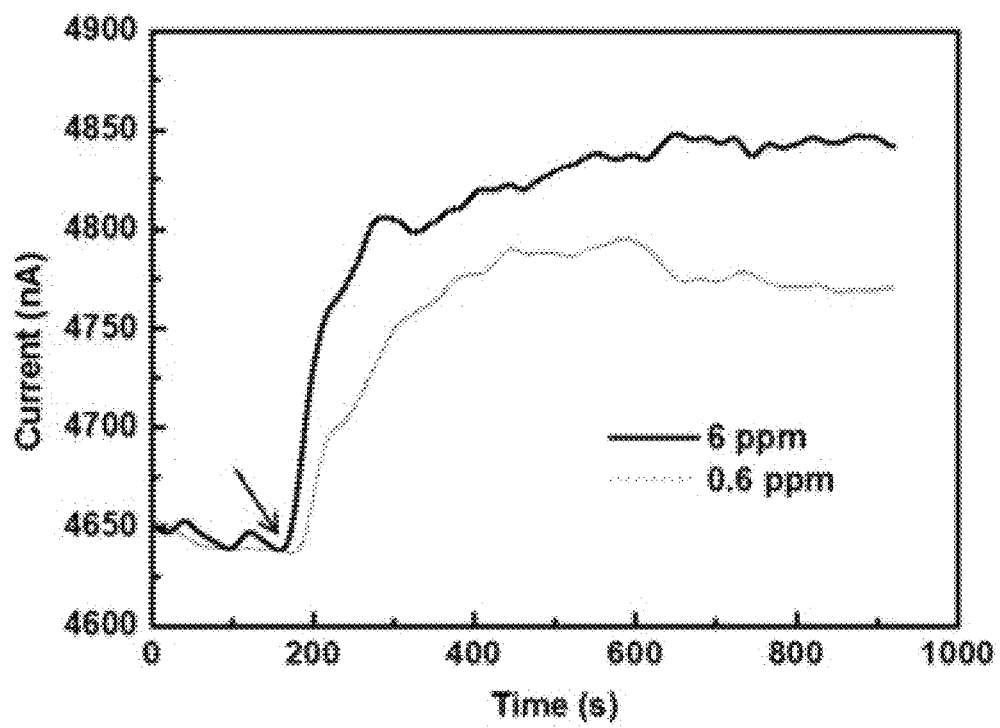
FIG. 5 shows a plot of current (nA) vs. time (s) in a graphite-based sensing device according to an embodiment of the present application for solutions with a chlorine concentration of 0.6 ppm or 6 ppm. The arrow in the plot represents the injection of the chlorine solution.

The PCAT-graphite sensor was then used in chlorine sensing by applying 10 mV and measuring the flow of current as it was exposed to various concentrations of free chlorine. The results of exposure to 6 ppm and 0.6 ppm free chlorine (flow rate: 0.2 mL/min) are shown in FIG. 5. The selected free chlorine sensing concentration range covers the whole range of free chlorine concentrations commonly present in drinking water. As shown in FIG. 5, the sensing performance of the graphite-based sensor is similar to the SWCNT-based sensor. During the measurement, the current was first stable at the baseline before sensing. The current showed a significant increase immediately after free chlorine flowed onto the sensor and contacts the PCAT-graphite film (flow rate was set as 0.1 mL/min). Similar to the PCAT-SWCNT device, the current gradually increased and then settled down to a stable value around 4850 nA for 6 ppm and 4750 nA for 0.6 ppm. Additionally, the sensor could also be reset by applying −0.8 V to reduce the PCAT back to its original state.

These results also indicate that other semiconductor-based or carbon-based materials such as iron oxide ($Fe_2O_3$), molybdenum disulfide ($MoS_2$), multiwall carbon nanotubes (MWCNTs), graphene and fullerene may also be able to be used as a substrate material for the sensors.

Example 4

Sensing Alternate Oxidant Species ($H_2O_2$ Sensing)

$H_2O_2$ is another commonly used oxidant in water treatment which can also sensed by the oxidant sensor of the present studies. However, the oxidation capacity of $H_2O_2$ is lower than free chlorine. Therefore a 1 mV biasing signal was used instead of 0.1 mV in order to amplify the current response.

Figure 6:
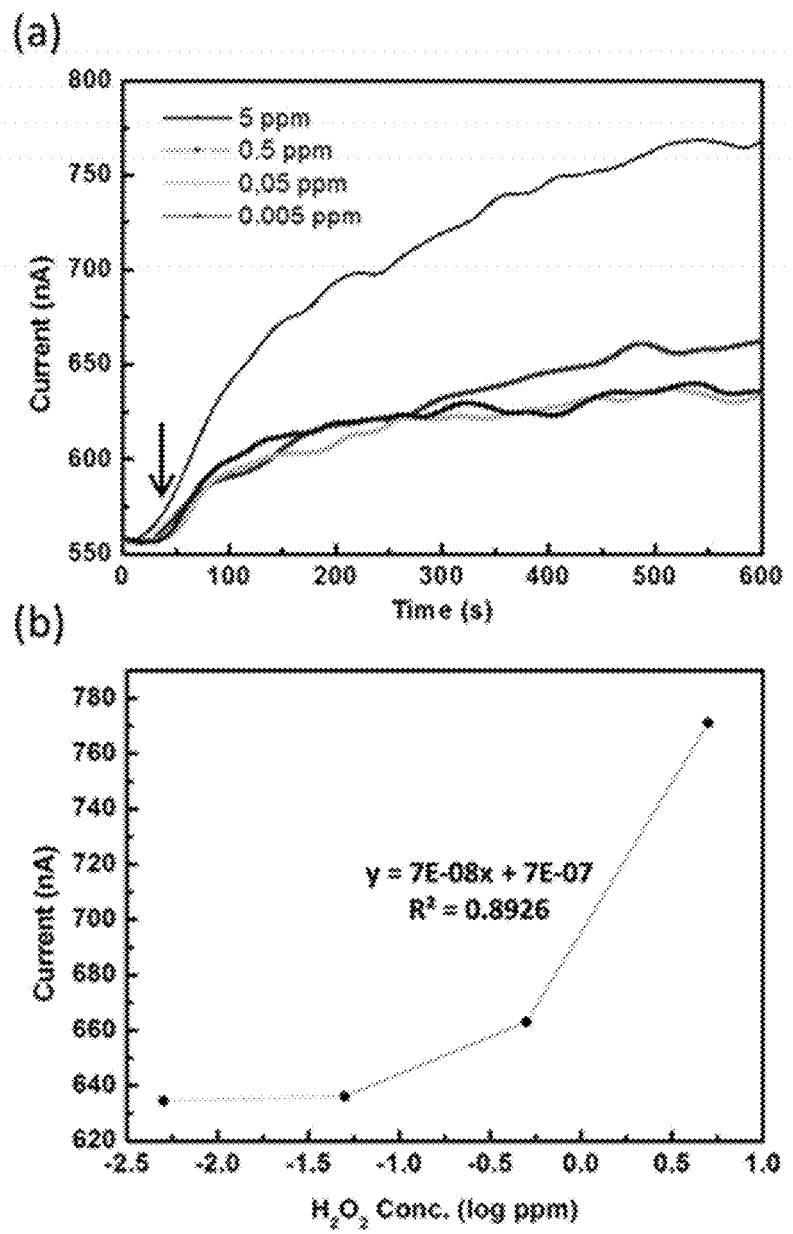
FIG. 6 shows (a) a plot of current (nA) vs. time (s) in a sensing device according to an embodiment of the present application for solutions with an $H_2O_2$ concentration from 0.005 ppm to 5 ppm. The arrow in the plot represents the injection of the $H_2O_2$ solution. (b) the relationship between the log $H_2O_2$ concentration and the current which is linear (solid line) for the $H_2O_2$ concentrations between 0.05 to 5 ppm ($R^2$=0.8926). The lighter gray line between 0.005 to 0.05 ppm represents the non-linear relationship of the log $H_2O_2$ concentration and the current in that range.

FIG. 6 shows the $H_2O_2$ sensing results of the PCAT-SWCNT device used in the present studies. As shown in FIG. 6(a), the measured current was stable at the baseline before sensing. The current variation of $H_2O_2$ sensing was similar to the chlorine sensing and showed a significant increase immediately after $H_2O_2$ flowed into the sensor and contacted the PCAT-SWCNT film (flow rate was set as 0.1 mL/min). Similar to the low concentration (0.06 ppm) chlorine sensing, the current gradually increased and then settled down to a stable value around 771 nA for 5 ppm, 663 nA for 0.5 ppm, 636 nA for 0.05 ppm and 634 nA for 0.005 ppm, respectively. The measured current was linearly proportional to the log of the $H_2O_2$ concentration in the range of 0.05-5 ppm (solid line) and the plot is shown in FIG. 6(b). This range is similar to the linear range of chlorine sensing which was 0.06 to 6 ppm. These results show that the current readings can be used to distinguish various $H_2O_2$ concentrations.

Example 5

Alternate Ligands for Selectivity (DPPD, ACAT)

In this sensor design, other phenyl capped oligomers such as amine capped aniline trimer (ACAT) and N,N'-diphenyl-p-phenylenediamine (DPPD) can also be used as the dopants for oxidant sensing.

Figure 7:
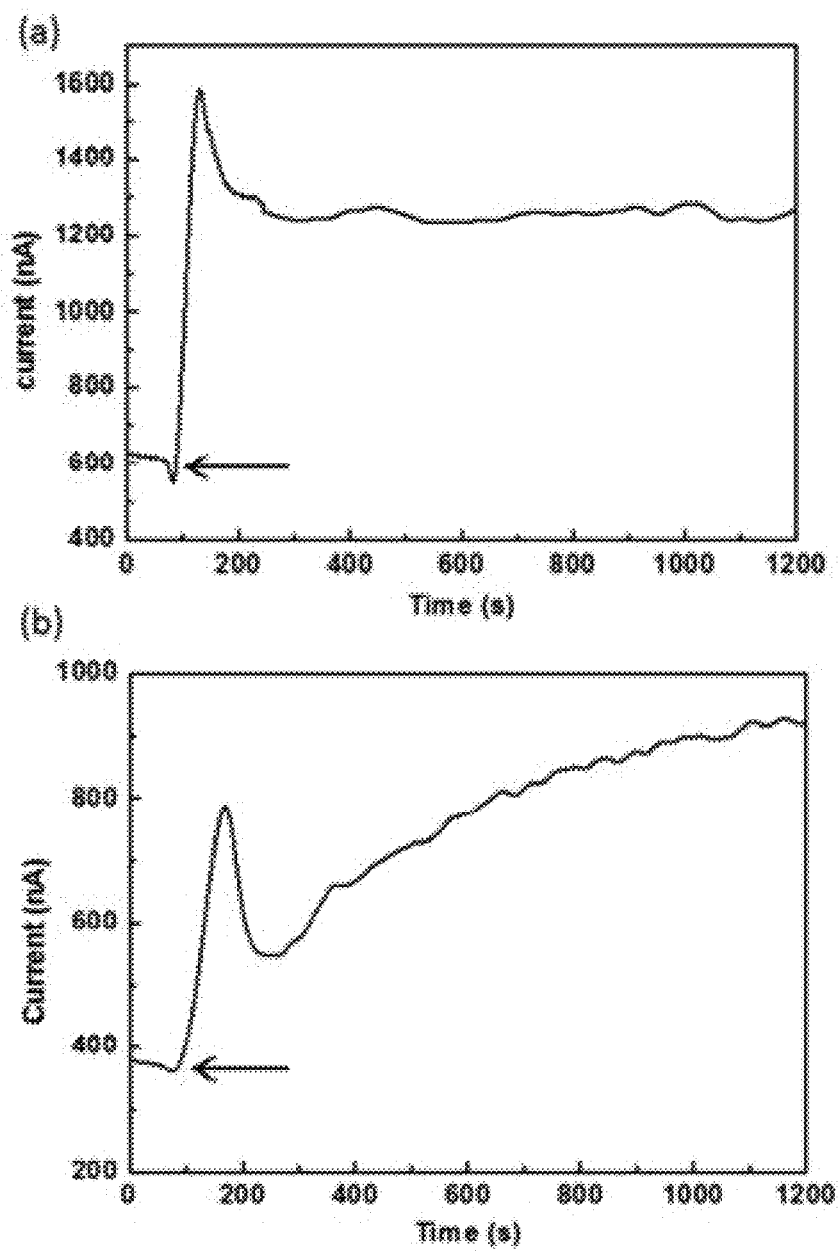
FIG. 7 shows a plot of current (nA) vs. time (s) in (a) amine capped aniline trimer (ACAT) and (b) N,N'-diphenyl-p-phenylenediamine (DPPD) based sensing devices according to embodiments of the present application for solutions with a chlorine concentration of from 0.6 ppm to 6 ppm. Arrows in the plots represent the injection of the chlorine solution.

FIG. 7 shows the 60 ppm free chlorine sensing results of the ACAT and DPPD based sensors. In these sensing experiments, all other operation parameters remained the same as the PCAT-based sensor described hereinabove in Example 1, namely, flow rate (0.1 mL/min) and applied potential (0.1 mV). As shown in FIG. 7, the measured current in both the ACAT and DPPD based devices were stable at the baselines (ACAT: 620 nA; DPPD: 375 nA) before sensing. The current variation of the ACAT device during sensing was similar to the PCAT device which showed a sharp increase upon the initial contact immediately after chlorine flowed into the sensor and contacted the ACAT-SWCNT film. Then the current settled down to a stable value at 1260 nA. The DPPD device showed a similar sensing behavior to the low concentration (0.06 ppm) chlorine sensing of the PCAT device, that is, the current gradually increased and then settled down to a stable value of around 900 nA.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE DESCRIPTION

[1] U.S. Environmental Protection Agency, *EPA Guidance Manual Alternative Disinfectants and Oxidants Chapter 2 DISINFECTANT USE IN WATER TREATMENT*, 1st ed. (U.S. Environmental Protection Agency, Washington, D.C., 1999), pp. 1-54.

[2] C. Federal-Provincial-Territorial Committee on Drinking Water, *Guidelines for Canadian Drinking Water Quality Guideline Technical Document—Chlorine* (Ottawa, 2009), pp. 1-39.

[3] D. L. Harp, *Current Technology of Chlorine Analysis for Water and Wastewater*, 1st ed. (Hach Company, Loveland, Colo., 1995), pp. 1-34.

[4] T. Nakagama, M. Yamada, and T. Hobo, Anal. Chim. Acta 231, 7 (1990).

[5] M. Zenki, H. Komatsubara, and K. Tôei, Anal. Chim. Acta 208, 317 (1988).

[6] K. Verma, A. Jain, and A. Townshend, Anal. Chim. Acta 261, 233 (1992).
[7] A. Okumura, A. Hirabayashi, Y. Sasaki, and R. Miyake, Anal. Sci. 17, 1113 (2001).
[8] F. Kodera, M. Umeda, and A. Yamada, Anal. Chim. Acta 537, 293 (2005).
[9] D. Pletcher and E. M. Valdes, Anal. Chim. Acta 246, 267 (1991).
[10] A. van den Berg, A. Grisel, E. Verney-Norberg, B. H. van der Schoot, M. Koudelka-Hep, and N. F. de Rooij, Sensors Actuators B Chem. 13, 396 (1993).
[11] F. J. Del Campo, O. Ordeig, and F. J. Muñoz, Anal. Chim. Acta 554, 98 (2005).
[12] C. Gutsche, Colloid Polym. Sci. 282, 1299 (2004).
[13] K. R. Moonoosawmy and P. Kruse, J. Am. Chem. Soc. 132, 1572 (2010).
[14] M. Baibarac, I. Baltog, S. Lefrant, J. Y. Mevellec, and O. Chauvet, Chem. Mater. 15, 4149 (2003).
[15] G. M. Do Nascimento, P. Corio, R. W. Novickis, M. L. a. Temperini, and M. S. Dresselhaus, J. Polym. Sci. Part A Polym. Chem. 43, 815 (2005).
[16] S. Srivastava, S. S. Sharma, S. Agrawal, S. Kumar, M. Singh, and Y. K. Vijay, Synth. Met. 160, 529 (2010).
[17] E. Hogue, T. Chowdhury, and P. Kruse, Submitted. (2015).
[18] Y. Xia and G. Whitesides, Angew. Chemie Int. Ed. 37, 550 (1998).
[19] C. Federal Provincial Territorial Committee on drinking water, *Guidelines for Canadian Drinking Water Quality Summary Table* (Ottawa, Canada, 2008), pp. 1-14.
[20] I. Kulszewicz-Bajer, I. Rozalska, and M. Kurylek, New J. Chem. 28, 669 (2004).
[21] H. Zhang, X. Wan, X. Xue, Y. Li, A. Yu, and Y. Chen, Eur. J. Org. Chem. 2010, 1681.

The invention claimed is:

1. A method for detecting an oxidant in a test liquid sample, the method comprising:
    obtaining a first resistance using a sensor in the presence of a blank liquid sample, wherein the sensor comprises:
    (a) a first electrode;
    (b) a second electrode opposed to the first electrode; and
    (c) a composite material between and connecting the first electrode and the second electrode, the composite material comprising a semiconductor and a redox-switchable organic compound adsorbed onto the semiconductor by physisorption, chemisorption, covalent attachment or ionic interaction; and
    obtaining a second resistance using the sensor in the presence of the test liquid sample;
    wherein a decrease in second resistance from the first resistance indicates the presence of the oxidant in the test liquid sample.

2. The method of claim 1, wherein the oxidant comprises free chlorine.

3. The method of claim 2, wherein the test liquid sample is drinking water.

4. The method of claim 1, wherein the first electrode, the second electrode and the composite material are provided on a substrate.

5. The method of claim 4, wherein the semiconductor is in the form of a layer that is grown in situ, vapour-deposited, drop-deposited, screen-printed, ink printed, abrasion-deposited or flow-deposited between the first and second electrodes.

6. The method of claim 1, wherein the first electrode and second electrode are graphite, gold, silver, copper, aluminium, titanium or indium tin oxide electrodes.

7. The method of claim 1, wherein the first electrode and second electrode are gold electrodes.

8. The method of claim 1, wherein the semiconductor is carbon nanotubes, graphene, graphite, fullerenes, iron oxide ($Fe_2O_3$) or molybdenum disulfide ($MoS_2$).

9. The method of claim 1, wherein the semiconductor is single wall carbon nanotubes (SWCNTs).

10. The method of claim 1, wherein the redox-switchable organic compound is an aniline oligomer or a pyrrole oligomer.

11. The method of claim 10, wherein the redox-switchable organic compound is phenyl capped aniline tetramer (PCAT), amine capped aniline tetramer (ACAT) or N,N'-diphenyl-p-phenylenediamine (DPPD).

12. The method of claim 1, wherein the sensor further comprises a microchannel for entry and exit of the liquid sample, the microchannel being in fluid contact with at least a portion of the composite material and not the first electrode and the second electrode.

13. The method of claim 1, wherein the sensor further comprises an insulator layer located between the first and second electrodes and the composite material.

14. The method of claim 1, wherein the sensor further comprises a counter electrode, reversibly couplable to the first or the second electrode.

15. A method for quantifying the concentration of an oxidant in a test liquid sample, the method comprising:
    obtaining a resistance using a sensor in the presence of the test liquid sample, wherein the sensor comprises:
    (a) a first electrode;
    (b) a second electrode opposed to the first electrode; and
    (c) a composite material between and connecting the first electrode and the second electrode, the composite material comprising a semiconductor and a redox-switchable organic compound adsorbed onto the semiconductor by physisorption, chemisorption, covalent attachment or ionic interaction; and
    comparing the resistance for the test liquid sample with resistance values for one or more standard liquid samples to determine the concentration of the oxidant in the test liquid sample, wherein the resistance for the test liquid sample is proportional to the concentration of the oxidant in the liquid sample and the greater the concentration of the oxidant in the test sample, the lower the resistance.

16. The method of claim 15, wherein the oxidant is free chlorine, the semiconductor is SWCNTs and the test potential voltage is about 0.1 mV.

17. The method of claim 15, wherein the method further comprises, after measuring the resistance or the test liquid sample, applying a reset voltage across a counter electrode and either the first or second electrode under conditions to reduce the redox-switchable organic compound.

18. The method of claim 17, wherein the reset voltage is about −0.8 V.

19. The method of claim 15, wherein the oxidant is free chlorine, the semiconductor is SWCNTs and the redox-switchable organic compound is phenyl capped aniline tetramer (PCAT), amine capped aniline tetramer (ACAT) or N,N'-diphenyl-p-phenylenediamine (DPPD).

* * * * *